(12) United States Patent
Gala et al.

(10) Patent No.: US 6,335,347 B1
(45) Date of Patent: Jan. 1, 2002

(54) ETHYL 4-(8-CHLORO-5,6-DIHYDRO-11 H-BENZO[5,6]CYCLOHEPTA[1,2-B]PYRIDIN-11-YLIDENE)-1-PIPERIDENE CARBOXYLATE POLYMORPH

(75) Inventors: Dinesh Gala, East Brunswick; Donald J. DiBenedetto, Whippany, both of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/169,109

(22) Filed: Oct. 8, 1998

Related U.S. Application Data

(60) Provisional application No. 60/062,031, filed on Oct. 10, 1997.

(51) Int. Cl.[7] .................... A61K 31/4545; C07D 401/04; A61P 37/08
(52) U.S. Cl. .............................................. 514/290; 546/93
(58) Field of Search .............................. 546/93; 514/290

(56) References Cited

U.S. PATENT DOCUMENTS 4,282,233 A * 8/1981 Vilani ............................ 424/267

FOREIGN PATENT DOCUMENTS

WO 95/01792 * 1/1995

* cited by examiner

*Primary Examiner*—Evelyn Mei Huang
(74) *Attorney, Agent, or Firm*—Thomas D. Hoffman

(57) ABSTRACT

A polymorph form 2 of ethyl 4(8-chloro-5,6,-dihydro-11H-benzo[5,6]cyclohepta[1,2-b]pyridin-11-ylidene)-1-piperidene carboxylate (hereinafter "loratadine") represented by the formula

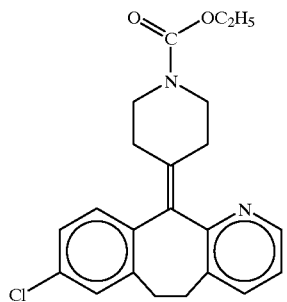

Pharmaceutical composition containing the polymorph form 2, and methods of using the polymorph form 2 to treat allergic reactions in mammals such as man are disclosed.

8 Claims, 3 Drawing Sheets

ETHYL 4-(8-CHLORO-5,6-DIHYDRO-11 H-BENZO[5,6]CYCLOHEPTA[1,2-B]PYRIDIN-11-YLIDENE)-1-PIPERIDENE CARBOXYLATE POLYMORPH

This application claims the benefit of provisional application 60/062,031 filed on Oct. 10, 1997.

Background of the Invention

This invention relates to a crystalline polymorph form 2 of ethyl 4-(8-chloro-5,6,-dihydro-11H-benzo[5,6]cyclohepta[1,2-b]pyridin-11- ylidene)-1-piperidene carboxylate (hereinafter "loratadine") represented by the formula

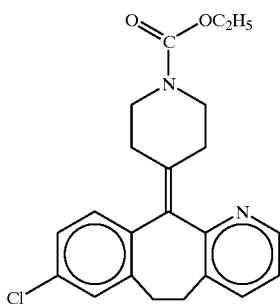

pharmaceutical compositions containing the polymorph form 2, and methods of using the polymorph form 2 to treat allergic reactions in mammals.

U.S. Pat. No. 4,282,233 discloses loratadine which possesses antihistaminic properties with substantially no sedative properties. This U.S. Pat. also discloses methods of making loratadine and using it to treat allergic reactions in mammals, but does not disclose or suggest the possible existence of a different polymorphic form.

To prepare pharmaceutical compositions containing loratadine for administration to mammals in accordance with exacting health registration requirements of the U.S. and international health registration authorities, e.g. the FDA's Good Manufacturing Practices ("GMP"), there is a need to produce loratadine in as stable a crystalline form as possible, especially a form having constant physical properties.

Summary of the Invention

We have discovered that loratadine can exist in the form of two distinct crystalline polymorphs, each having distinctly different physical properties.

Accordingly, this invention provides crystalline polymorph form 2 loratadine aracterized by the following x-ray powder diffraction pattern expressed in terms of "d" spacing and relative intensities("RI"):

| d spacing (±0.05) | RI |
|---|---|
| 10.12 | Medium |
| 5.65 | Strong |
| 5.08 | Medium |
| 4.29 | Strong |
| 3.99 | Very Strong |

This invention also provides crystalline polymorph form 2 loratadine characterized by the following x-ray powder diffraction pattern expressed in terms of "d" spacings and relative intensities ("RI")(s=strong, m=medium, w=weak, v=very and d=diffuse)

| d spacing | RI |
|---|---|
| 8.95 | W |
| 7.19 | W |
| 6.64 | M |
| 6.37 | W |
| 5.99 | W |
| 5.82 | VWD |
| 5.64 | W |
| 5.00 | VWD |
| 4.70 | M |
| 4.59 | VWD |
| 4.52 | W |
| 4.44 | M |
| 4.38 | M |
| 4.28 | VWD |
| 4.24 | W |
| 4.16 | VS |
| 3.71 | W |
| 3.66 | W |
| 3.62 | W |
| 3.57 | W |
| 3.50 | M |
| 3.44 | VW |
| 3.36 | S |
| 3.22 | W |
| 3.18 | W |
| 3.14 | VW |
| 3.10 | W |
| 3.03 | M |
| 2.98 | VWD |
| 2.93 | VWD |
| 2.86 | VWD |
| 2.83 | W |
| 2.79 | W |
| 2.73 | VWD |
| 2.70 | VWD |
| 2.64 | WD |
| 2.57 | VWD |
| 2.55 | VWD |
| 2.51 | VWD |
| 2.46 | VWD |
| 2.43 | VWD |
| 2.41 | VWD |
| 2.34 | WD |
| 2.32 | VWD |
| 2.30 | VWD |
| 2.27 | W |

Detailed Description of the Invention

We have discovered that loratadine can exists as two distinctly different polymorphs designated as form 1-loratadine prepared as described in U.S. Pat. No. 4,282,233 - and crystalline polymorph form 2 of loratadine prepared in accordance with the procedures of ths invention.

We have discovered specific solvents and experimental conditions which produce a distinctly different polymorph form 2 of loratadine Dissolution colorimetry shows more energy in the form of heat is needed to dissolve loratadine from 2 than that for from 1. These results suggest that crystalline loratadine polymorph form 2 should be more stable and create more stable dosage forms especially crystalline dosage forms compared to those for loratadine form 1. This is surprising in that loratadine form 1 is more stable and melts at 134° C and form 2 shows a transition to form 1 at about 118° C ; the sample then melts at 133° C, the melting point of loratadine form 2.

In the course of developing a pure loratadine polymorph form 2 for a pharmaceutical composition prepared in compliance with exacting GMP regulations, we discovered that crystallization of loratadine(prepared as described in U.S. Patent No. 4,282,233) from toluene, t-butyl methyl ether, heptane or mixtures thereof, produced pure polymorph form 2 loratadine (see Example 1). Use of a t-butyl methyl ether-toluene mixture is preferred.

The infrared spectrum of polymorph form 2 loratadine taken on as a mull in mineral oil dispersion is characterized by the following seven peaks not found in polymorph form 1:

| freguency (cm$^{-1}$) |
| --- |
| 1334 |
| 1279 |
| 1263 |
| 1032 |
| 802 |
| 570 |
| 549 |

Figure 1A:
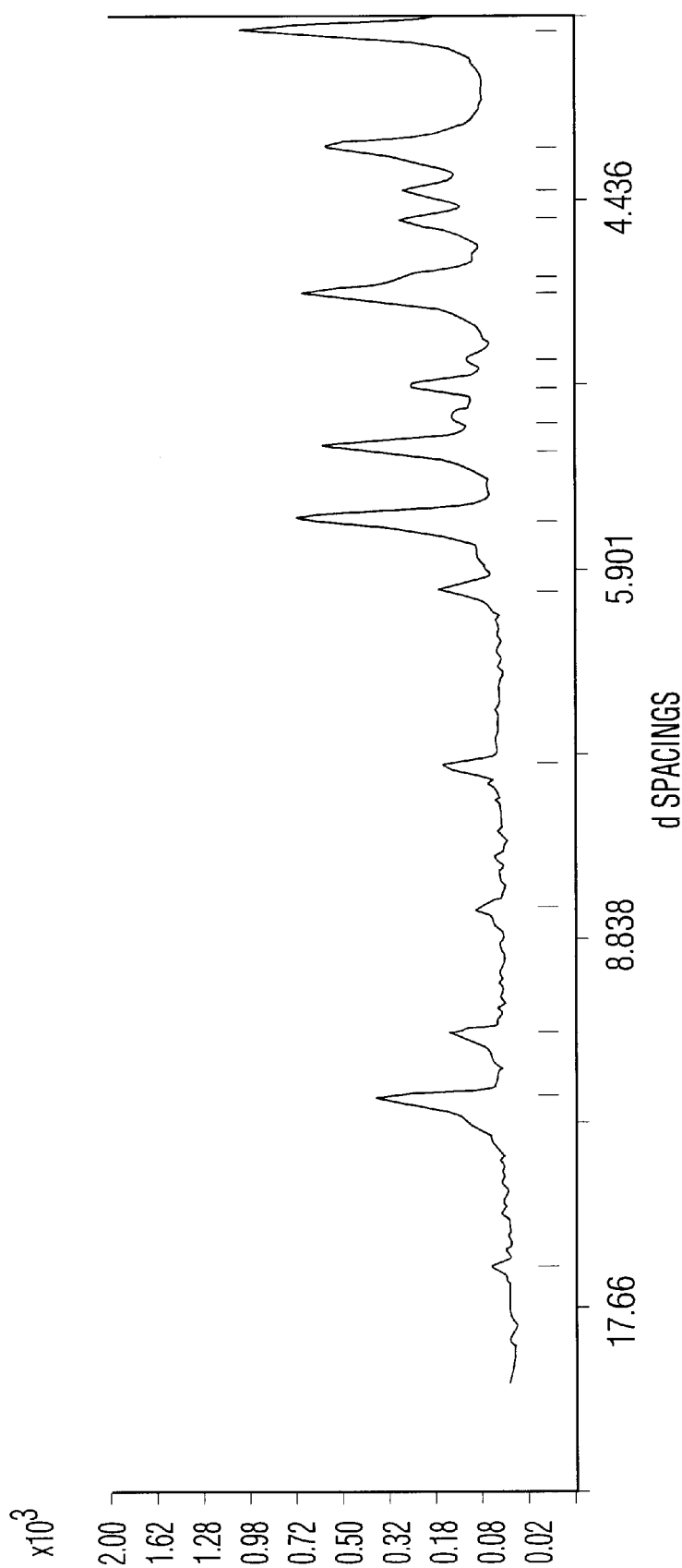
FIGS. 1A and 1B present a x-ray spectrum of crystalline polymorph form 2 loratadine
Figure 1B:
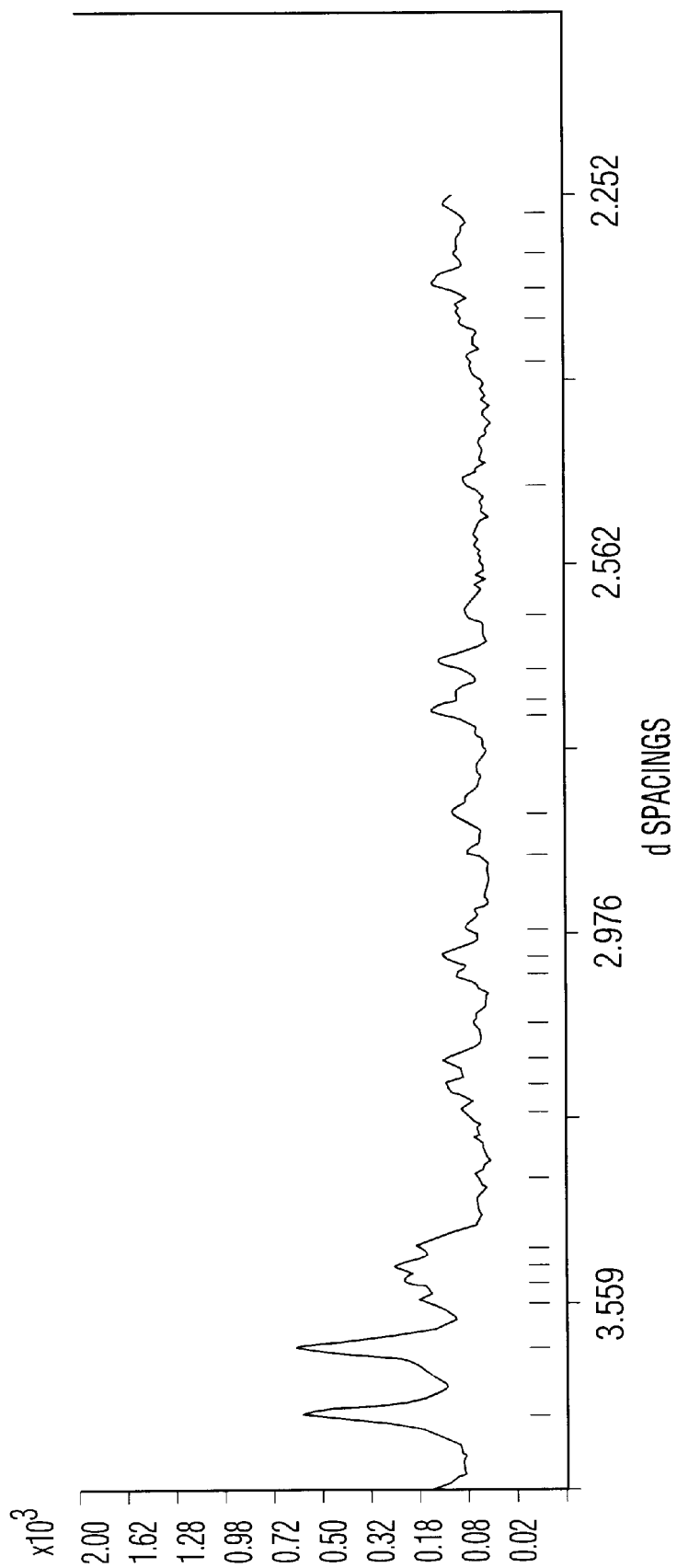
Figure 2:
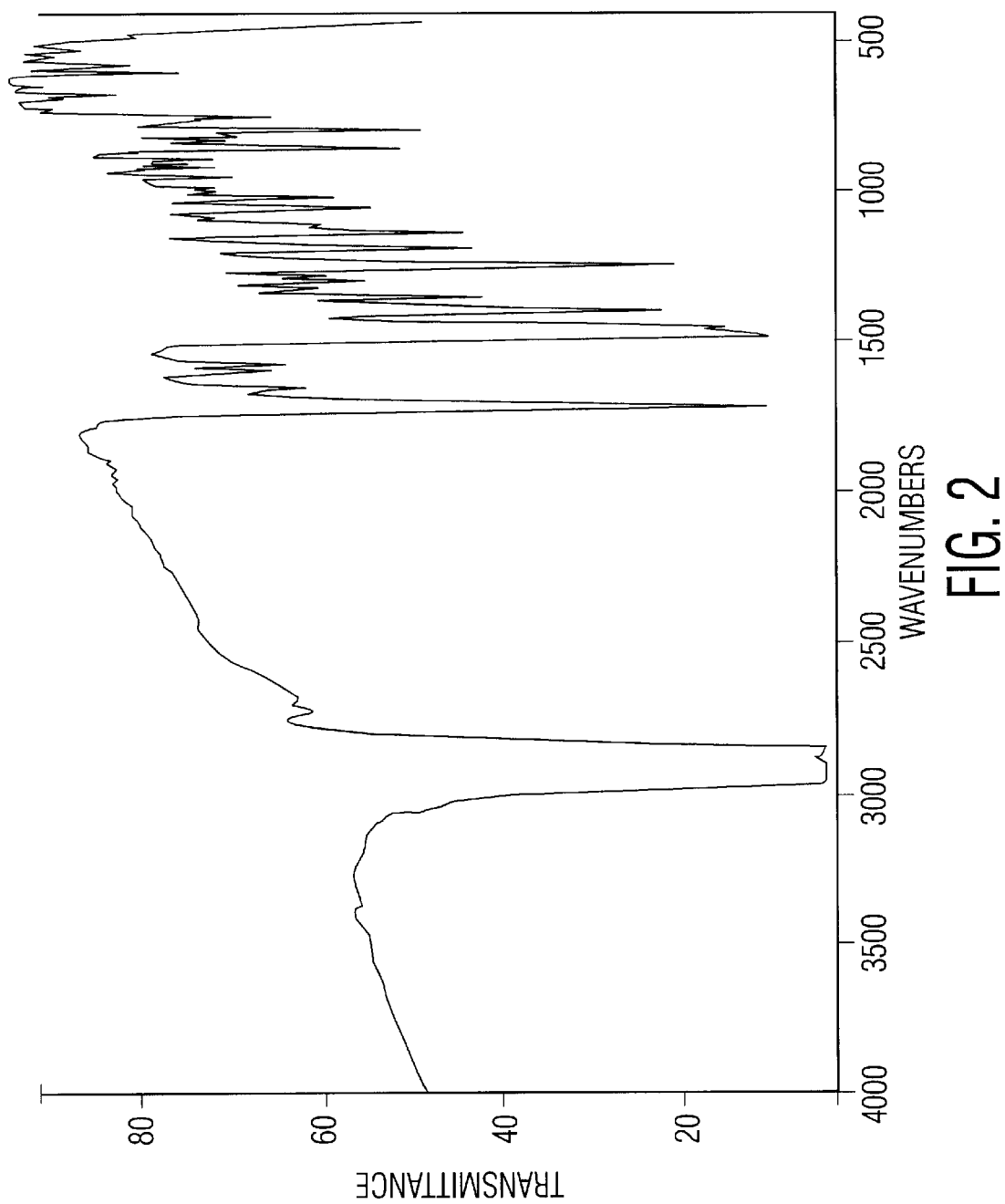
FIG. 2 presents the infrared spectrum of crystalline polymorph form 2 loratadine as a mull in mineral oil (Nujol) dispersion on a Mattson Galaxy 6021 FTIR spectrometer.

The complete infrared spectrum of polymorph form 2 loratadine taken as a mull in mineral oil dispersion is displayed in FIG. 2.

The infrared spectrum was obtained on a Mattson Galaxy 6021 FTIR spectrometer. The mull was prepared in accordance with the USP procedure <197M>. See also "Experiments in Techniques of Olnfrared Spectroscopy", R.W. Hannah and J. S. Swinehart, Perkin-Elmer Corpation, September,1974, pps, 6-1 to 6-6.

The x-ray powder diffraction pattern was measured on a Philips APD3720 automated diffractometer system (model PW 1800). The radiation source was copper (K-alpha) and the long fine focus tube connected to a Philips XRG 3100 x-ray generator operated at 45 KV and 40 mA. The take-off angle was 6 degrees and a graphite monochromator as used. A scintillation detector was employed and data was acquired with a scan rate of 0.025 degrees per second, a step size of 0.010 and a step time of 40 seconds per degree.

The x-ray powder diffraction pattern distinctive for polymorph form 2 loratadine expressed in terms of the following distinctive "d" spacing and relative intensties("RI") is provided hereinbelow:

| "d" spacings (+0.05) | RI |
| --- | --- |

A more complete x-ray powder diffraction pattern for polymorph form 2 loratadine expressed in "d" spacings and relative intensities("RI")is provided hereinbelow:

Pharmaceutical Compositions

Pharmaceutical compositions of this invention may contain in addition to an anti-allergically effective amount of polymorph form 1 loratadine as the active ingredient, inert pharmaceutically acceptable carriers that may be solids or liquids. Solid form compositions include powders, tablets, dispersible granules, capsules, cachets, and suppositories. A solid carrier can be one or more substances which may also act as diluants, flavoring agents, solubilizers, lubricants, suspending agents, binders or tablet disintegration agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from about 5 to about 20 percent of the active ingredient. Suitable solid carriers are magnesium carbonate, magnesium stearate, talc, sugar, lactose, pectin, dextrin, starch, gelatin, tragacanth, methycelulose, sodium carboxymethyl-cellulose, a low melting wax. cocoa butter and the like. The term "compositions" is intended to include the formulation of the active compound with encapsulating material as carrier providing a capsule in which the active component (with or without other carriers) is surrounded by carrier, which is thus in association with it. Similarly, caches are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for topical administration. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can e made by dispersing the finely divided active component in water with viscous material, i.e., natural or synthetic gums, resins, methylcellulose, sodium carboxymethylcellulose and other well-known suspending agents.

Topical formulation useful for nasal or ophthalmic administration are also contemplated. Topical formulation suitable for nasal administration may be solutions or suspensions. Ophthalmic formulations may be solutions, suspension or ointments. Ointments usually contain lipophilic carriers such as mineral oil and/or petrolatum. Solution for ophthalmic administration may contain sodium chloride, acid and/or base to adjust the pH as well as purified water and preservatives.

The anti-allergic effective amount of polymorph form 2 loratadine for topical administration varies from 0.1 to 5% by weight of the total pharmaceutical composition. The preferred amount varies from 0.5 to 2% by weight of the total pharmaceutical composition.

The anti-allergic effective amount of polymorph form 2 loratadine for oral administration varies from about 1 to 50 mg/day, preferably about 2.5 to 20 mg/day and more preferably about 5 to 10 mg/day in single or divided doses. The most preferred amount is 5.0 mg, once a day.

Of course the precise dosage and dosage regimen may be varied depending upon the requirements of the patients. (e.g.. his or her sex, age) as well as the severity of the allergic condition being treated. Determination of the proper dosage and dosage regimen for a particular patient will be within the skill of the attending clinician.

The polymorph form 2 loratadine possess antihistaminic properties. These antihistaminic properties have been demonstrated in standard animal models, such as prevention of histamine - induced lethality in guinea pigs. Antihistaminic activity of form 2 has also been demonstrated in a monkey model.

Example 1

Preparation of polymorph form 2 loratadine.

Dissolve loratadine (available from Schering Corporation, Kenilworth, NJ, see also U.S. Patent No. 4,282,233) in hot toluene and reflux for about 10-15 minutes. Cool the solution to 60-65° and add t-butylmethyl ether at this temperature. Stir at 60-65° for about 15 minutes and then cool the mixture to 0-5° C. Slowly add additional t-butylmethyl ether and cool the mixture to -3 to -10° C. Stir for about 1-6 hours at this temperature, filter, wash with cold (-5 to -10C) t-butylmethyl ether. Dry the solid under suction and then in a vacuum oven at 45-55° C to a constant weight.

What is claimed is:

1. Polymorph form 2 loratadine having by the following x-ray powder diffraction pattern expressed in terms of "d" spacing and relative intensities("RI"):

| d spacing (±0.05) | RI |
| --- | --- |
| 8.95 | Weak |
| 6.37 | Weak |
| 5.64 | Weak. |

2. Polymorph form 2 loratadine having by the following x-ray powder diffraction pattern expressed in terms of "d" spacing and relative intensities("RI") (s=strong, m=medium, w=weak, v=very and d=diffuse)

| d spacing | RI |
| --- | --- |
| 8.95 | W |
| 7.19 | W |
| 6.64 | M |
| 6.37 | W |
| 5.99 | W |
| 5.82 | VWD |
| 5.64 | W |
| 5.00 | VWD |
| 4.70 | M |
| 4.59 | VWD |
| 4.52 | W |
| 4.44 | M |
| 4.38 | M |
| 4.28 | VWD |
| 4.24 | W |
| 4.16 | VS |
| 3.71 | W |
| 3.66 | W |
| 3.62 | W |
| 3.57 | W |
| 3.50 | M |
| 3.44 | VW |
| 3.36 | S |
| 3.22 | W |
| 3.18 | W |
| 3.14 | VW |
| 3.10 | W |
| 3.03 | M |
| 2.98 | VWD |
| 2.93 | VWD |
| 2.86 | VWD |
| 2.83 | W |
| 2.79 | W |
| 2.73 | VWD |
| 2.70 | VWD |
| 2.64 | WD |
| 2.57 | VWD |
| 2.55 | VWD |
| 2.51 | VWD |
| 2.46 | VWD |
| 2.43 | VWD |
| 2.41 | VWD |
| 2.34 | WD |
| 2.32 | VWD |
| 2.30 | VWD |
| 2.27 | W. |

3. A pharmaceutical composition comprising an anti-allergic effective amount of the polymorph form 2 loratadine of claim 1 and a pharmaceutically acceptable carrier.

4. A pharmaceutical composition comprising an anti-allergic effective amount of the polymorph form 2 loratadine of claim 2 and a pharmaceutically acceptable carrier.

5. The polymorph form 2 loratadine of claim 1 further having by an infrared spectrum generated on a mull of polymorph form 2 in mineral oil showing the following peaks:

| frequency (cm$^{-1}$) |
| --- |
| 1334 |
| 1279 |
| 1263 |
| 1032 |
| 802 |
| 570 |
| 549. |

6. A method of treating allergic reactions in a mammal which comprises administering to said mammal an anti-allergic effective amount of the polymorph form 2 loratadine of claim 1.

7. The polymorph form 2 loratadine of claim 1 further having by an infrared spectrum displayed in FIG. 2.

8. A method of treating allergic reactions in a mammal which comprises administering to said mammal an anti-allergic effective amount of the polymorph form 2 loratadine of claim 2.

* * * * *